(12) United States Patent
Shioda (10) Patent No.: US 8,258,477 B2
(45) Date of Patent: Sep. 4, 2012

(54) INSPECTION APPARATUS AND INSPECTION METHOD

(75) Inventor: Michinori Shioda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 333 days.

(21) Appl. No.: 12/626,251

(22) Filed: Nov. 25, 2009

(65) Prior Publication Data

US 2010/0148071 A1    Jun. 17, 2010

(30) Foreign Application Priority Data

Dec. 12, 2008   (JP) ................................ 2008-316415
Nov. 13, 2009   (JP) ................................ 2009-260108

(51) Int. Cl.
    *G01J 5/02*       (2006.01)
(52) U.S. Cl. .................................................. 250/341.1
(58) Field of Classification Search .................... 702/73; 250/341.1
    See application file for complete search history.

(56) References Cited

U.S. PATENT DOCUMENTS

| | | | |
|---|---|---|---|
| 5,939,721 A | 8/1999 | Jacobsen et al. | 250/330 |
| 2006/0227340 A1 | 10/2006 | Shioda et al. | 356/614 |
| 2011/0184654 A1* | 7/2011 | Ben-David et al. | 702/19 |

FOREIGN PATENT DOCUMENTS

JP         H10-153547         6/1998

OTHER PUBLICATIONS

Chin Cheng Te, et al: "Investigation of biomaterial classification using T-rays", Proceedings of SPIE, vol. 4937, Dec. 16, 2002, pp. 294-306, XP007905719.

Weng, et al: "Discriminating DNA Sequences from Terahertz Spectroscopy—A Wavelet Domain Analysis", IEEE Bioengineering Conference, Apr. 2006, pp. 211-212, XP010915990.

Galvão, et al: "Optical discrimination and classification of THz spectra in the wavelet domain", Optics Express, vol. 11, No. 12, Jun. 16, 2003, pp. 1462-1473, XP002639653.

Handley, et al: "Wavelet compression in medical terahertz pulsed imaging", Physics in Medicine and Biology, vol. 47, No. 21, Nov. 7, 2002, pp. 3885-3892, XP55001136.

Shon, et al: "Compression of Pulsed Terahertz Image Using Discrete Wavelet Transform", Japanese Journal of Applied Physics, vol. 46, No. 12, Jan. 2007, pp. 7731-7736, XP55001141.

Pittner, et al: "Feature Extraction From Wavelet Coefficients for Pattern Recognition Tasks", IEEE Transactions on Pattern Analysis and Machine Intelligence, vol. 21, No. 1, Jan. 1999, pp. 83-88, XP000803257.

(Continued)

*Primary Examiner* — Constantine Hannaher
(74) *Attorney, Agent, or Firm* — Fitzpatrick, Cella, Harper & Scinto (57) ABSTRACT

An inspection apparatus for inspecting a subject (sample) (for example, performing identification or imaging of the subject) using an expansion coefficient with a relatively small amount of data. The inspection apparatus includes a transforming unit that performs a wavelet transform on a terahertz time waveform obtained using a terahertz wave detected by a detecting unit. In addition, the inspection apparatus includes a selecting unit that selects, from a first expansion coefficient in the wavelet transform, a second expansion coefficient stored in advance and included in the first expansion coefficient. Furthermore, the inspection apparatus includes a comparing unit for comparing a first value of the second expansion coefficient with a second value of the second expansion coefficient selected by the selecting unit.

9 Claims, 4 Drawing Sheets

OTHER PUBLICATIONS

Yinsheng, Qu et al: "Data Reduction Using a Discrete Wavelet Transform in Discriminant Analysis of Very High Dimensionality Data", Biometrics, vol. 59, No. 1, Mar. 2003, pp. 143-151, XP55001144.

Mittleman, et al: "Gas Sensing Using Terahertz Time-Domain Spectroscopy", Applied Physics B: Lasers and Optics, vol. B67, No. 3, Sep. 1, 1998, pp. 379-390, XP000783019.

European Search Report dated Jul. 13, 2011 in corresponding European Application No. 09178633.5.

B. Ferguson, et al., "De-noising techniques for terahertz responses of biological samples", Microelectronics Journal 32, pp. 943-953, (2001).

* cited by examiner

INSPECTION APPARATUS AND INSPECTION METHOD

BACKGROUND OF THE INVENTION

1. Field of the Invention

The present invention relates to an inspection apparatus and an inspection method for inspecting a subject using a terahertz wave. In the present specification, an electromagnetic wave having a frequency range including at least a portion of a range from 30 GHz to 30 THz, inclusive, is referred to as a terahertz wave.

2. Description of the Related Art

Conventionally, Fourier analysis has been used to study the frequency dependence of an absorption rate and a refractive index of a sample (subject) from a time waveform of a terahertz wave transmitted through or reflected off of the sample.

However, in a wide frequency range included in the time waveform of a terahertz wave, the frequency dependence of an absorption rate and a refractive index is unique to each material. In this case, an increase in the amount of data to be compared becomes problematic.

In order to solve the problem described above, Japanese Patent Application Laid-Open No. H10-153547 discloses a method for compressing dispersion-related information included in a time waveform of a terahertz wave into a small amount of data and identifying components of a material from the compressed data. Japanese Patent Application Laid-Open No. H10-153547 discloses the use of wavelet analysis as a compression method thereof.

SUMMARY OF THE INVENTION

However, Japanese Patent Application Laid-Open No. H10-153547 fails to disclose a specific method of performing wavelet analysis. In particular, no disclosure is made on wavelet expansion coefficients.

An object of the present invention is to inspect a subject (sample) (for example, identifying or imaging the subject) using an expansion coefficient with a relatively small amount of data.

The present invention is directed to an inspection apparatus for inspecting a subject, comprising: an irradiating unit for irradiating the subject with a terahertz wave; a detecting unit for detecting a terahertz wave obtained from the subject; a transforming unit for performing a wavelet transform on a time waveform of the terahertz wave obtained using the terahertz wave detected by the detecting unit; a selecting unit for selecting a second expansion coefficient stored in advance from a first expansion coefficient in the wavelet transform and included in the first expansion coefficient; and a comparing unit for comparing a first value of the second expansion coefficient to a second value of the second expansion coefficient selected by the selecting unit.

The second expansion coefficient can be an expansion coefficient obtained using a reference object having a characteristic part of spectrum and related to the characteristic part of spectrum, the inspection apparatus comprising a determining unit for determining, based on a result obtained by the comparing unit, whether the subject is the reference object or not.

The present invention is directed to an inspection method for inspecting a subject, comprising: irradiating the subject with a terahertz wave; detecting a terahertz wave obtained from the subject; performing a wavelet transform on a time waveform of the terahertz wave obtained using the terahertz wave detected in the detecting step; selecting a second expansion coefficient stored in advance from a first expansion coefficient in the wavelet transform and included in the first expansion coefficient; and comparing a first value of the second expansion coefficient and a second value of the second expansion coefficient selected in the selecting step.

The second expansion coefficient can be an expansion coefficient obtained using a reference object having a characteristic part of spectrum and which is related to the characteristic part of spectrum, the inspection method comprising determining, based on a result obtained in the comparing step, whether the subject is the reference object or not.

The present invention is directed to a computer-readable storage medium storing a program that causes a computer to execute the inspection method.

The present invention is directed to a program that causes a computer to execute the inspection method.

The present invention is directed to an extraction method for extracting, from a reference object having a characteristic part of spectrum, an expansion coefficient related to the characteristic part of spectrum, the extraction method comprising: acquiring the waveform of a terahertz wave reflected or scattered off of or transmitted through the reference object; performing a wavelet transform on a terahertz time waveform acquired in the acquiring step; performing an inverse wavelet transform on a portion of expansion coefficients in the wavelet transform; performing a Fourier transform on the terahertz time waveform acquired in the inverse-transforming step, wherein the inverse-transforming step and the second transforming step are repeatedly performed while changing the portion of the expansion coefficients.

In the extraction method, performing the inverse waveform transform can include setting a threshold when specifying the portion of the expansion coefficient, the extraction method arranged so as to replace a value of the expansion coefficient that is equal to or greater than the set threshold or equal to or smaller than the set threshold by zero.

In consideration of the problem described above, an apparatus according to the present invention is an apparatus for obtaining information on a subject with a spectrum including a characteristic spectrum part, and features the following characteristics. The apparatus includes an irradiating unit that irradiates the subject with a terahertz wave, a detecting unit that detects a terahertz wave from the subject irradiated with the terahertz wave, a transforming unit, and a comparing unit. The transforming unit performs a wavelet transform on a terahertz time waveform (a time waveform of a terahertz wave) acquired based on a signal detected by the detecting unit. The comparing unit compares a value, stored in advance, of a wavelet expansion coefficient related to a characteristic part of spectrum of a subject having a spectrum including a characteristic part of spectrum with a value at the same coefficient position as the wavelet expansion coefficient stored in advance among the values of wavelet expansion coefficients acquired by the transforming unit.

In addition, in consideration of the problem described above, a method according to the present invention is a method for obtaining information on a subject with a spectrum including a characteristic spectrum part, and features the following characteristics. The method includes an irradiating step in which the subject is irradiated with a terahertz wave, a detecting step in which a terahertz wave is detected from the subject irradiated with the terahertz wave, a transforming step, an extracting step, and a comparing step. In the transforming step, a wavelet transform is performed on a terahertz time waveform acquired based on a signal detected by the detecting unit. In the extracting step, a wavelet expansion coefficient related to a characteristic part of spectrum of a subject having a spectrum including a characteristic part of spectrum is extracted. In the comparing step, a value of the wavelet expansion coefficient extracted in the extracting step is compared with a value at the same coefficient position as the extracted wavelet expansion coefficient among the values of wavelet expansion coefficients acquired in the transforming step. In addition, in the extracting step, an inverse wavelet transform is performed by replacing a portion of the wavelet expansion coefficient decomposed by the wavelet transform performed in the transforming step with zero. Subsequently, Fourier transform is performed on a terahertz time waveform obtained by the inverse wavelet transform to find a wavelet expansion coefficient that alters the characteristic part of spectrum.

Furthermore, in consideration of the problem described above, an extraction method according to the present invention for extracting a wavelet expansion coefficient related to a characteristic part of spectrum includes an acquiring step, a transforming step, and an extracting step. In the acquiring step, a time waveform of a terahertz wave from a subject with a spectrum including a characteristic part of spectrum is acquired. In the transforming step, a wavelet transform is performed on the terahertz time waveform acquired in the acquiring step. In the extracting step, a wavelet expansion coefficient related to a characteristic part of spectrum of a subject having a spectrum including a characteristic part of spectrum is extracted. In addition, in the extracting step, an inverse wavelet transform is performed by replacing a portion of the wavelet expansion coefficient decomposed by the wavelet transform performed in the transforming step with zero. Subsequently, Fourier transform is performed on a terahertz time waveform acquired by the inverse wavelet transform to find a wavelet expansion coefficient that alters the characteristic part of spectrum.

The apparatus and the method (inspection apparatus and inspection method) according to the present invention enables a value of a stored wavelet expansion coefficient related to a characteristic part of spectrum to be compared with a value at the same coefficient position as the stored wavelet expansion coefficient among values of wavelet expansion coefficients acquired by the transforming unit. Alternatively, a wavelet transform can be performed on a terahertz time waveform to extract a wavelet expansion coefficient related to a characteristic part of spectrum.

Accordingly, a subject (sample) can typically be inspected (for example, identification or imaging of the subject can be performed) using a wavelet expansion coefficient with a relatively small amount of data. By handling a relatively small amount of data, inspection speed can be increased.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

(Inspection Apparatus)

Figure 1A:
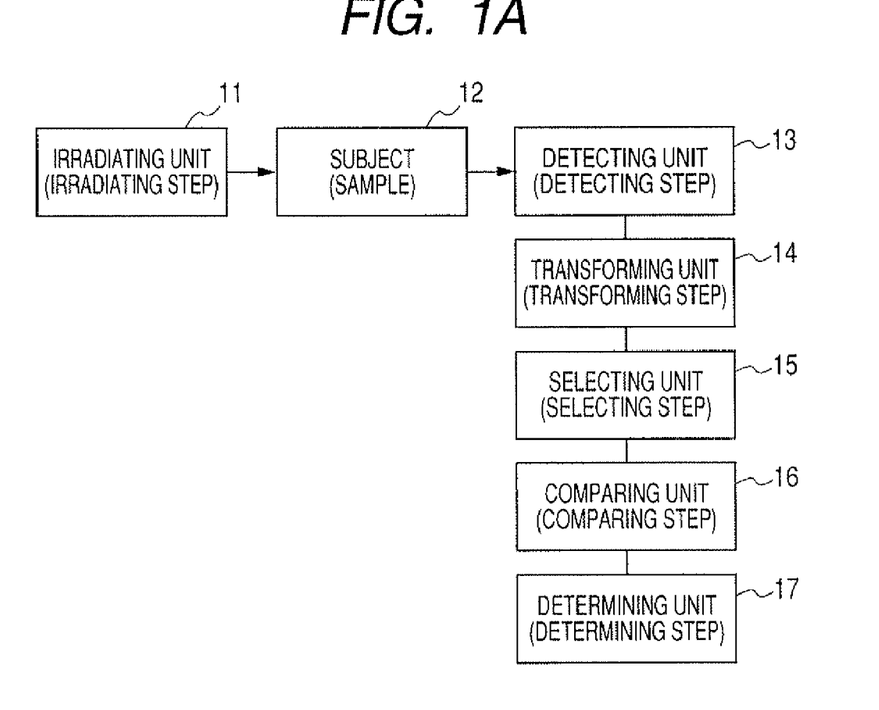
FIGS. 1A and 1B are schematic diagrams for describing a configuration of an inspection apparatus according to an embodiment.

An inspection apparatus (an inspection apparatus for inspecting a subject) according to an embodiment will now be described with reference to FIG. 1A.

The inspection apparatus according to the present embodiment includes an irradiating unit 11 (for example, made up of a photoconductive device) that irradiates a subject 12 (sample) with a terahertz wave.

In addition, the inspection apparatus includes a detecting unit 13 (for example, made up of a photoconductive device) that detects a terahertz wave from the subject 12 irradiated with a terahertz wave. In this case, the detecting unit 13 detects a terahertz wave obtained from the subject 12. That is, the detecting unit detects a terahertz wave reflected or scattered off of or transmitted through the subject 12.

In addition, the inspection apparatus includes a transforming unit 14 that performs a wavelet transform on a terahertz time waveform (for example, the waveform illustrated in FIG. 2A) acquired based on a signal detected by the detecting unit 13. In this case, the transforming unit 14 performs a wavelet transform on a time waveform (for example, the waveform illustrated in FIG. 2A) of the terahertz wave obtained using the terahertz wave detected by the detecting unit 13.

Figure 3A:
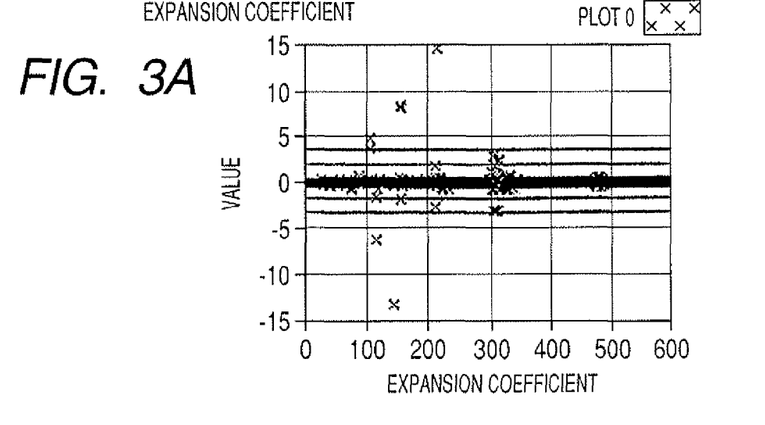
FIGS. 3A, 3B, and 3C are schematic diagrams for describing first and second examples.
Figure 3B:
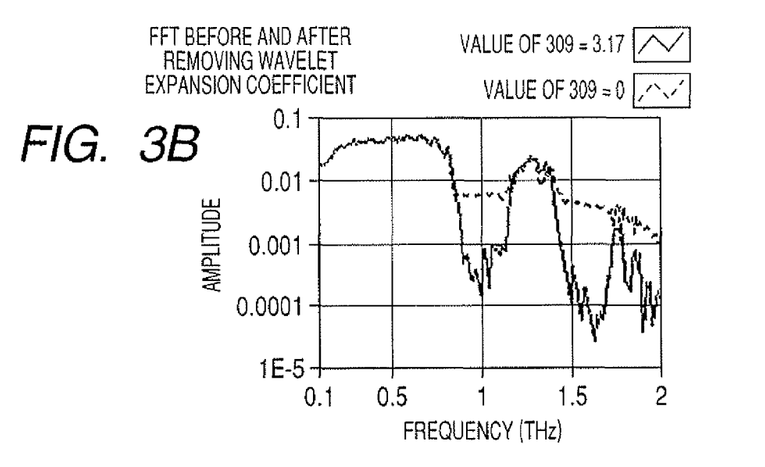

In addition, the inspection apparatus includes a selecting unit 15 that selects, from a first expansion coefficient (for example, the abscissa of FIG. 3A) in the wavelet transform, a second expansion coefficient stored in e.g. a semiconductor memory in advance and included in the first expansion coefficient, which second expansion coefficient is, for example, a 309th wavelet expansion coefficient determined in FIG. 3B which is an expansion coefficient related to a characteristic part of spectrum obtained using a reference object having a characteristic part of spectrum such as an absorption spectrum.

Furthermore, the inspection apparatus includes a comparing unit 16 for comparing a first value (for example, 3.17 in the case of the 309th wavelet expansion coefficient determined in FIG. 3B) of the second expansion coefficient with a second value (the value of the 309th wavelet expansion coefficient with respect to the subject 12) of the second expansion coefficient selected by the selecting unit 15.

Accordingly, the subject 12 can typically be inspected (for example, identification or imaging of the subject can be performed) using a wavelet expansion coefficient with a relatively small amount of data. By handling a relatively small amount of data, inspection speed can be increased. Here, the inspection refers to a comparison performed between a reference object (for example, a pharmaceutical product) and a different object (the subject 12) that is the same type as the reference object. Accordingly, the subject can be identified.

In this case, the inspection apparatus preferably includes a determining unit 17 that determines, based on a result obtained from the comparing unit 16, whether the subject 12 is the reference object.

(Extracting Unit)

In the configuration described above, typically, the inspection apparatus preferably includes an extracting unit for extracting a wavelet expansion coefficient related to the characteristic part of spectrum. The extracting unit extracts a coefficient position and a value of a wavelet expansion coefficient related to a characteristic part of spectrum of an object with a spectrum including the characteristic part of spectrum stored in advance.

In addition, in this case, a wavelet expansion coefficient related to a characteristic part of spectrum can also be extracted with respect to the subject using the extracting unit to compare a value of the extracted wavelet expansion coefficient with a value of the wavelet expansion coefficient stored in advance.

The extracting unit performs, for example, an inverse wavelet transform by replacing, with zero, a portion selected based on a given criterion of the wavelet expansion coefficient decomposed by the wavelet transform performed by the transforming unit. Subsequently, Fourier transform is performed on a terahertz time waveform acquired by the inverse wavelet transform to find a wavelet expansion coefficient that alters the characteristic part of spectrum.

In addition, a wavelet expansion coefficient with a high correlation (degree of incidence) with a characteristic part of spectrum may be extracted. This method utilizes a property that the presence or absence of a wavelet expansion coefficient strongly correlated with a characteristic part of spectrum determines whether or not a time waveform acquired by an inverse wavelet transform has a characteristic part of spectrum.

To ensure that the comparison and extraction are performed appropriately, for example, the transforming unit uses a mother wavelet strongly correlated to a terahertz waveform, and performs a wavelet transform on the terahertz time waveform so that the characteristic part of spectrum is to be associated with a part of the wavelet expansion coefficient.

The apparatus can be used to determine whether a subject is an object with a spectrum having a characteristic part of spectrum in order to construct a screening system for screening a subject based on the determination.

(Inspection Method)

In addition, another inspection method according to the present embodiment (an inspection method for inspecting a subject) includes the steps a) to e) described below.

a) An irradiating step 11 for irradiating a subject 12 with a terahertz wave.
b) A detecting step 13 for detecting a terahertz wave from the subject 12 irradiated with the terahertz wave. Alternatively, a detecting step 13 for detecting a terahertz wave reflected or scattered off of or transmitted through the subject 12.
c) A transforming step 14 for performing a wavelet transform on a terahertz time waveform acquired based on a signal detected in the detecting step 13. Alternatively, a transforming step 14 for performing a wavelet transform on a time waveform of the terahertz wave obtained using the terahertz wave detected in the detecting step 13.
d) A selecting step 15 for selecting a second expansion coefficient (an expansion coefficient related to a characteristic part of spectrum obtained using a reference object having a characteristic part of spectrum) stored in advance from a first expansion coefficient obtained in the transforming step 14.
e) A comparing step 16 for comparing a value of the wavelet expansion coefficient selected in the selecting step 15 with a value at the same coefficient position as the extracted wavelet expansion coefficient among the values of wavelet expansion coefficients acquired in the transforming step 14. Alternatively, a comparing step 16 for comparing a first value of the second expansion coefficient stored in advance and a second value of the second expansion coefficient selected in the selecting step 15.

The inspection method preferably includes a determining step for determining, based on a result obtained in the comparing step 16, whether the subject 12 is the reference object.

(Extracting Step)

In addition, the inspection method preferably includes an extracting step for performing an inverse wavelet transform by replacing, with zero, a portion of the wavelet expansion coefficient decomposed by the wavelet transform performed in the transforming step. In this case, a Fourier transform is performed on a terahertz time waveform acquired by the inverse wavelet transform to find a wavelet expansion coefficient that alters the characteristic part of spectrum.

In the extracting step, for example, a value of a wavelet expansion coefficient equal to or greater than a threshold or equal to or smaller than the threshold is replaced by zero and a process such as an inverse wavelet transform is performed, whereby the process is executed every time the threshold is varied. Consequently, a wavelet expansion coefficient that causes the characteristic part of spectrum to vary is found.

In addition, a wavelet expansion coefficient with a high correlation (degree of incidence) with a characteristic part of spectrum may be extracted. This method utilizes a property that the presence or absence of a wavelet expansion coefficient strongly correlated with a characteristic part of spectrum determines whether or not a time waveform acquired by an inverse wavelet transform has a characteristic part of spectrum.

In the extracting step, a wavelet expansion coefficient that causes the characteristic part of spectrum to vary can be found by executing the process after replacing values of the wavelet expansion coefficient in a specified coefficient position range with zero and executing the process every time the range is varied.

The inspection method can further include a saving step and a restoring step described below. In the saving step, when the subject is determined in the comparing step to be an object with a spectrum having the characteristic part of spectrum, a value of a wavelet expansion coefficient having almost no signal components and which expresses noise is replaced with zero or a small value. An information-compressed wavelet expansion coefficient is then saved. In the restoring step, an inverse wavelet transform is performed on the information-compressed wavelet expansion coefficient saved in the saving step to restore the terahertz time waveform of the subject. Based on the terahertz time waveform of the subject restored in the restoring step, an absorption rate or a refractive index can be determined to execute an imaging step for performing imaging of the subject. The SN ratio of the restored terahertz time waveform can be improved even when using data with an inferior SN ratio acquired at high speed. Therefore, imaging can be executed in a favorable manner at high speed.

(Extraction Method)

Another embodiment of the present invention will be described.

A wavelet expansion coefficient related to a characteristic part of spectrum (or a fingerprint spectrum) is extracted using an appropriate method. The appropriate method involves studying whether or not a change in the wavelet expansion coefficient causes a change in the characteristic part of spectrum and extracting a wavelet expansion coefficient that causes such change. In other words, a candidate wavelet expansion coefficient is set to zero, an inverse wavelet transform is performed thereon, and a Fourier transform is performed on the obtained terahertz time waveform. A determination is made on whether a characteristic part of spectrum of the spectrum obtained by the Fourier transform has changed or not, whereby a wavelet expansion coefficient that has caused a change is extracted as a target wavelet expansion coefficient.

In addition, another extraction method according to the present embodiment (an extraction method for extracting, from a reference object having a characteristic part of spectrum, an expansion coefficient related to the characteristic part of spectrum) includes the following steps.

The method includes an acquiring step, a transforming step, and an extracting step. In the acquiring step, a time waveform of a terahertz wave from a subject with a spectrum including a characteristic part of spectrum is acquired. In the transforming step, a wavelet transform is performed on the terahertz time waveform acquired in the acquiring step (first transforming step). In the extracting step, a wavelet expansion coefficient related to a characteristic part of spectrum of an object having a spectrum including a characteristic part of spectrum is extracted. In addition, in the extracting step, an inverse wavelet transform is performed by replacing a portion of the wavelet expansion coefficient decomposed by the wavelet transform performed in the transforming step with zero (inverse-transforming step). A Fourier transform is then performed on the terahertz time waveform obtained by the inverse wavelet transform (second transforming step). The inverse-transforming step and the second transforming step are repeated while changing a portion of the expansion coefficient. Consequently, a wavelet expansion coefficient that causes the characteristic part of spectrum to vary is found.

EXAMPLES

Next, specific examples of an inspection apparatus and method using a wavelet expansion coefficient related to a characteristic absorption spectrum that is an example of a spectrum having a characteristic part of spectrum will be described. A characteristic absorption spectrum may sometimes be referred to as a fingerprint spectrum in the terahertz range. When obtaining a fingerprint spectrum, typically, a terahertz wave in a range from 30 GHz to 30 THz, inclusive, that includes a frequency component within a range from 0.1 THz to 10 THz, inclusive, is used.

In the following examples, a method will be described in which a terahertz time waveform whose data had been acquired at high speed is decomposed into wavelet expansion coefficients by a wavelet transform and a wavelet expansion coefficient related to a characteristic absorption spectrum is extracted from the wavelet expansion coefficients. Subsequently, an inspection apparatus and method will be described which determine, using the wavelet expansion coefficient related to the characteristic absorption spectrum, whether a sample is a substance having the characteristic absorption spectrum.

The examples of the present invention to be described below are related to the inspection of a sample having a characteristic absorption spectrum in the terahertz range. A photonic crystal will be described as an example of such samples. The used photonic crystal has two characteristic absorption spectra in the terahertz range.

Figure 4A:
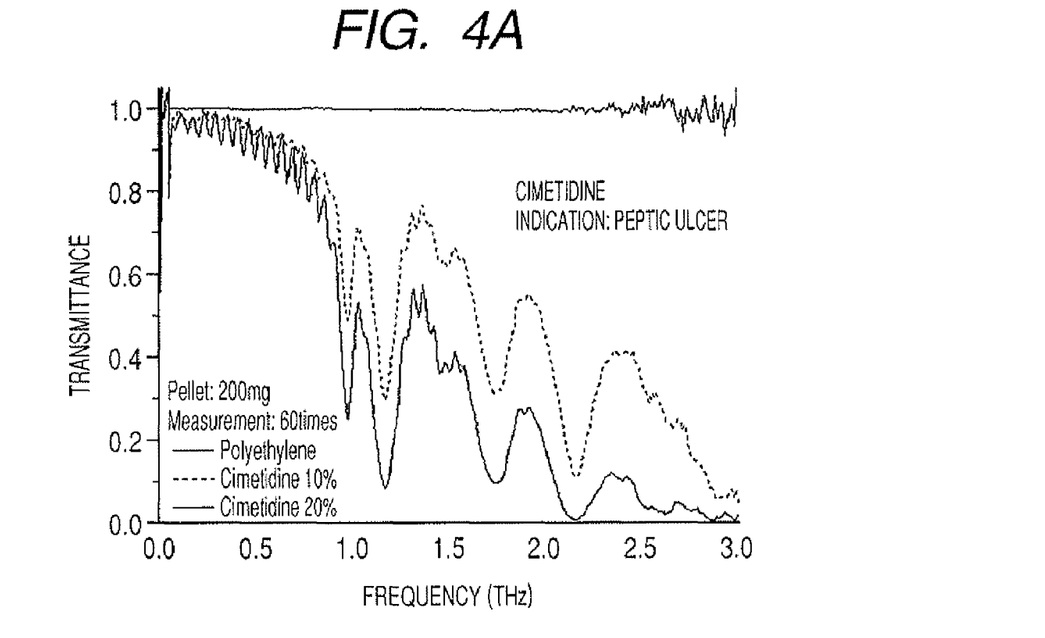
FIGS. 4A and 4B are schematic diagrams for illustrating spectra of pharmaceutical products.
Figure 4B:
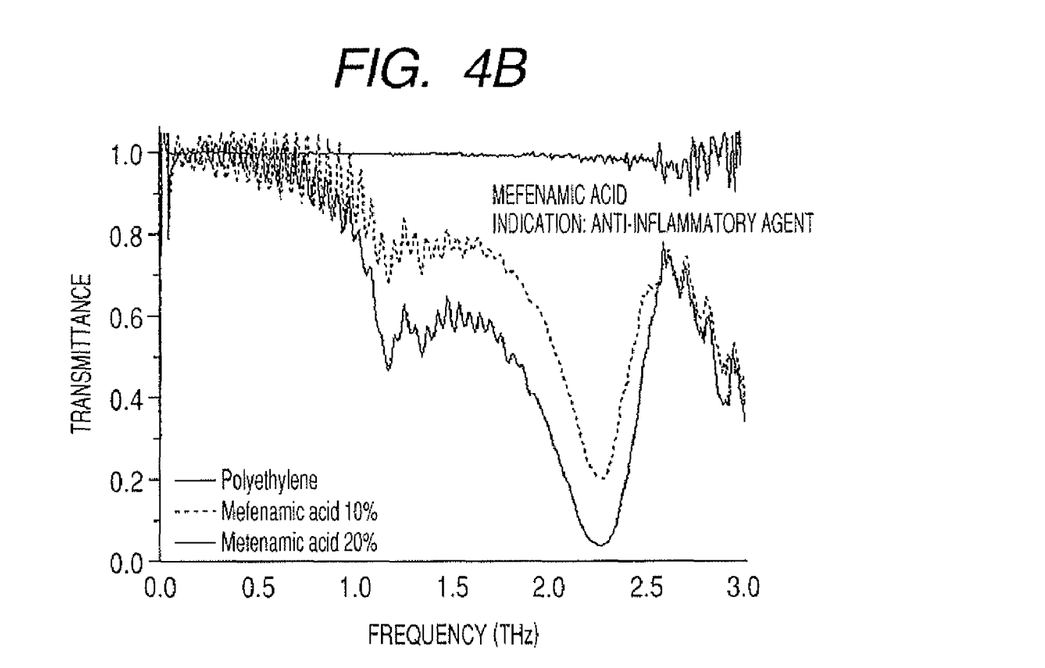

While an example using a photonic crystal will be described below, the present invention is generally applicable to any material having a fingerprint spectrum. For example, the present invention can also be applied to pharmaceutical products (cimetidine, mefenamic acid, chlorpropamide, lansoprazole), hormonal molecules (progesterone, dopamine, acetylcholine, estriol), environmental endocrine disrupters (amitrole, benzophenone), sugars (maltose, glucose), and the like. As examples, the fingerprint spectra of cimetidine and mefenamic acid are respectively illustrated in FIGS. 4A and 4B. These examples show that characteristic absorption spectra exist in a frequency range from near 0.1 THz to near 2.5 THz.

First Example

Figure 1B:
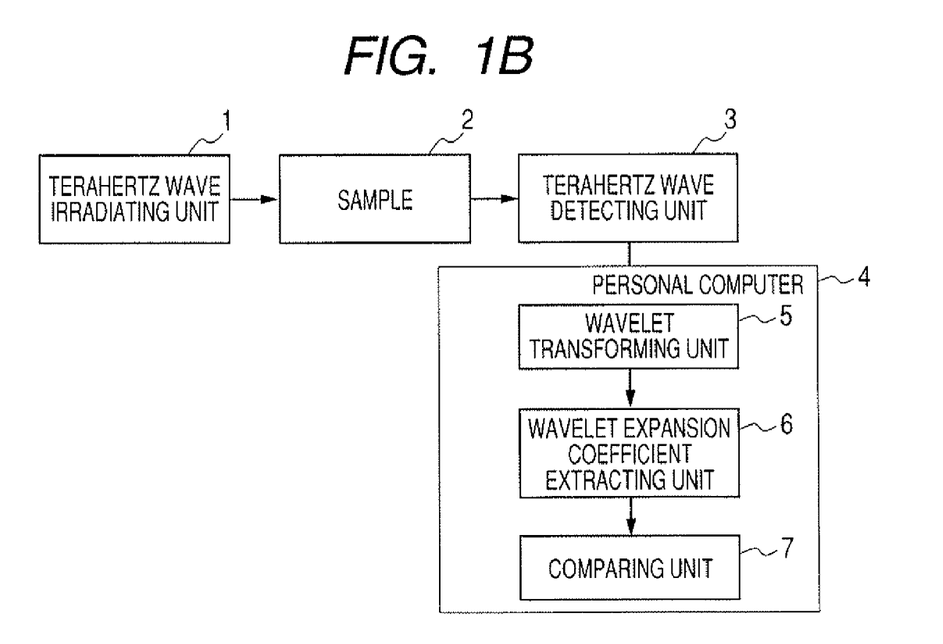

FIG. 1B is a schematic diagram of a configuration of a first example.

A terahertz wave irradiating unit 1 irradiates a sample 2 with a generated terahertz wave. In addition, a terahertz wave detecting unit 3 detects a terahertz wave transmitted through the sample. A personal computer 4 loads a signal detected by the terahertz wave detecting unit 3.

As the terahertz wave irradiating unit 1, a unit that generates a terahertz wave using a photoconductive device can be used. In addition, a unit that detects a terahertz wave using a photoconductive device can also be used as the terahertz wave detecting unit 3. The photoconductive device used herein is capable of generating and detecting a terahertz wave whose frequency ranges from 0.1 THz to 2.5 THz, inclusive.

A method of generating and detecting a terahertz wave using a photoconductive device is known as THz-TDS (terahertz time-domain spectrometry). A signal obtained by the terahertz wave detecting unit 3 is a terahertz wave time waveform. A terahertz wave time waveform can be obtained by scanning a delay system (not explicitly shown in FIG. 1B) made up of a stage. However, in order to improve SN ratio, the stage is slowly scanned and signals at respective points on the stage are aggregated. Therefore, the acquisition of a terahertz wave time waveform takes time.

Alternatively, the stage is first scanned at high speed. When doing so, a time waveform of a terahertz wave for which only a small number of data units can be acquired for averaging at the respective data acquisition points is to be acquired at high speed. Next, time waveforms of the terahertz wave having a small number of data units are repeatedly acquired. The time waveforms of the terahertz wave are added up and averaged for denoising (improving the SN ratio). In this case, since the time waveform of the terahertz wave is repeatedly measured, averaging to ultimately shape a time waveform of the terahertz wave with a favorable SN ratio is time-consuming.

Conventionally, a Fourier transform is performed on a time waveform of a terahertz wave with a favorable SN ratio measured slowly in this manner and spectrum distributions are compared to determined whether a measured sample has a characteristic absorption spectrum or not. However, due to the wide frequency range and a greater amount of data to be compared, the method is impractical. As shown, a conventional method requires time to acquire a time waveform of a terahertz wave to be used in the Fourier transform. In addition, the amount of data to be compared which is used to determine whether a measured sample has a characteristic absorption spectrum or not also increases.

In consideration thereof, the present invention is configured such that a determination of whether or not a measured sample has a characteristic absorption spectrum can be made even on a time waveform of a terahertz wave acquired at high speed. Specifically, for example, a stage of a delay system is scanned at high speed, a time waveform of a terahertz wave with a relatively small number of data units (with an unfavorable SN ratio) is acquired over a short period of time, the data is loaded into the personal computer 4 and decomposed into wavelet expansion coefficients by a unit 5 that performs a wavelet transform (transforming unit). By using a mother wavelet strongly correlated with the terahertz time waveform, a terahertz wave that is a signal component can be separated from noise with relative ease. "Strongly correlated" means having a shape resembling the terahertz time waveform so as to enable a description using a small number of wavelet expansion coefficients as possible. In this case, the number of data units Ls of the terahertz wave time waveform was set to Ls=4096 (=$2^{12}$) and Coiflet4 was used as the mother wavelet. In addition, the level at which the number of wavelet expansion coefficients are to be decided was set to $\log_2 Ls=12$, which is the maximum number in this case.

Next, an extraction method performed by a unit 6 (extracting unit) for extracting a wavelet expansion coefficient related to a characteristic absorption spectrum will be described. When a wavelet expansion coefficient obtained by a wavelet transform is subjected as-is (without making any changes to the respective wavelet expansion coefficients) to an inverse wavelet transform, a time waveform of a terahertz wave prior to the wavelet transform is obtained. However, in this case, the following operation is to be performed. First, a threshold is set to a value near zero (a relatively small value). Subsequently, for example, an inverse wavelet transform is performed using a wavelet expansion coefficient having the same value as the set threshold or a smaller value than the set threshold. In other words, values greater than the set threshold are replaced by zero and an inverse wavelet transform is performed using a wavelet expansion coefficient having a value (not replaced by zero). The waveform obtained by the inverse wavelet transform is then subjected to a Fourier transform.

In a similar manner, the same process is performed by slightly increasing the value of the set threshold. By incrementally increasing the value of the threshold and observing the change in the spectrum due to Fourier transforms, it is found that a significant change of a characteristic absorption spectrum such as a disappearance or appearance thereof sometimes occurs when the value of the threshold changes. Calculating the difference between wavelet expansion coefficients corresponding to preceding and subsequent thresholds at that point enables a wavelet expansion coefficient causing a significant change in the characteristic absorption spectrum to be found. A position and a value of the wavelet expansion coefficient causing the significant change in the characteristic absorption spectrum found in this manner are saved.

Figure 2A:
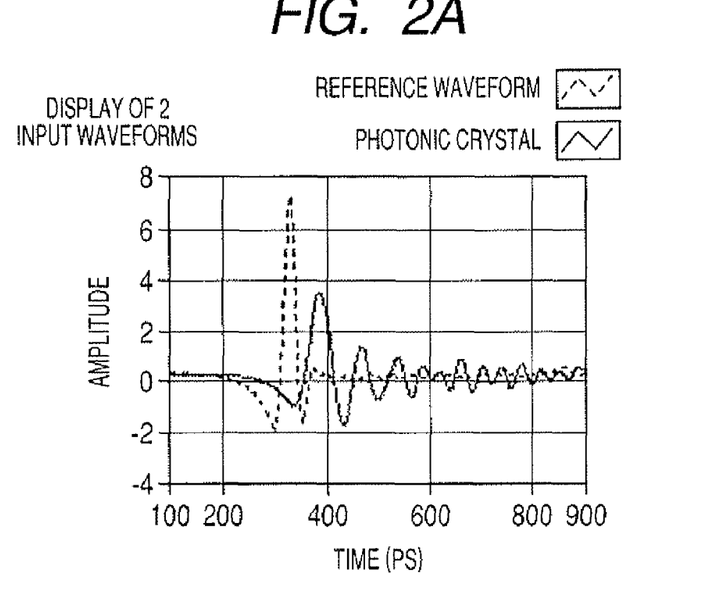
FIGS. 2A and 2B are schematic diagrams illustrating time waveforms of terahertz waves respectively acquired when a sample is not available and when a sample is available, and respective Fourier transforms thereof.

FIG. 2A illustrates a reference waveform (dashed line) that is a time waveform of a terahertz wave when a sample is not available and a time waveform (solid line) of a terahertz wave when a photonic crystal having a characteristic absorption spectrum in the terahertz range is used as a sample.

Figure 2B:
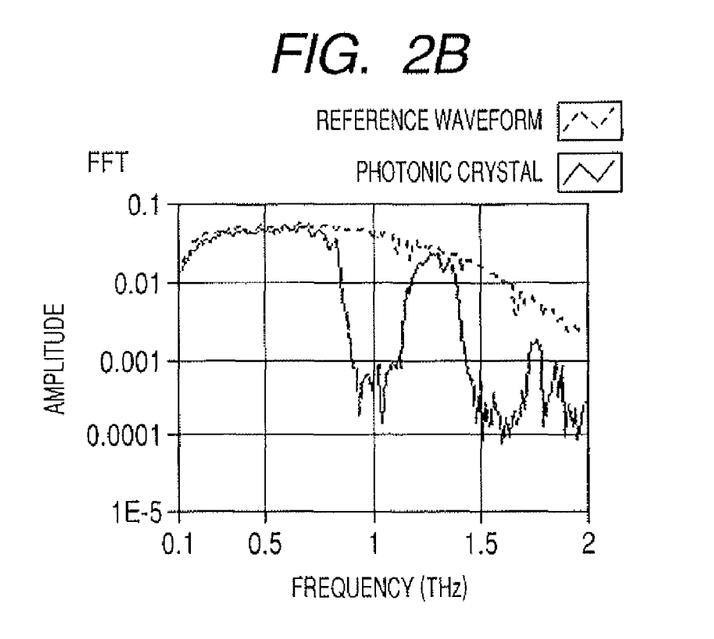

FIG. 2B illustrates spectra resulting from Fourier transforms respectively performed on the waveforms. The spectrum (solid line) with drops near 1 THz and near 1.6 THz is a Fourier transform of a terahertz wave time waveform when the photonic crystal is used as a sample, while the spectrum (dashed line) without the absorption spectrum is a Fourier transform of the reference waveform.

FIG. 3A is a graphical representation of a portion of wavelet expansion coefficients resulting from a wavelet transform performed on the terahertz wave time waveform when the photonic crystal is used as a sample. As described earlier, Coiflet4 was used as the mother wavelet and the level was set to $\log_2 Ls=12$ (the number of signal data units Ls was set to Ls=4096). A region enclosed by a square near values 5 and −5 of the ordinate in FIG. 3A is a schematic graphical representation of differences in wavelet expansion coefficients before and after a change when thresholds whose absolute values are the same are incrementally varied. If there is a difference in spectra before and after thresholds whose absolute values are the same are varied, the change in the spectra is due to a wavelet expansion coefficient included in the region enclosed by the square. Therefore, by diversely varying the threshold to change the region enclosed by the square and extracting a wavelet expansion coefficient included in the region, a relationship between the wavelet expansion coefficient and spectrum changes can be studied. The region may include a plurality of wavelet expansion coefficients if the variation width of the threshold is significant. By setting a small threshold variation width, the region enclosed by the square can be reduced and the number of wavelet expansion coefficients related to a characteristic absorption spectrum can be narrowed down. From the perspective of increasing data processing speed, the smaller the number of wavelet expansion coefficients related to the characteristic absorption spectrum, the better.

A study performed in this manner on a wavelet expansion coefficient related to a characteristic absorption spectrum with respect to the photonic crystal revealed that the value of wavelet expansion coefficient number 309 is a wavelet expansion coefficient related to the characteristic absorption spectrum. While the value of the expansion coefficient number 309 takes a value of 3.17 when the characteristic absorption spectrum is present, the absorption spectrum of the characteristic absorption spectrum disappears dramatically when the value is changed to zero. The solid line in FIG. 3B represents a spectrum when expansion coefficient number 309 takes a value of 3.17 and a characteristic absorption spectrum exists.

On the other hand, the dashed line in FIG. 3B represents a spectrum when the value of the expansion coefficient number 309 is set to zero. It is shown that the spectrum has disappeared dramatically. Therefore, first, in this manner, with respect to a sample having a characteristic absorption spectrum, a position and a value of a wavelet expansion coefficient related to the characteristic absorption spectrum is checked in advance. Subsequently, the same wavelet transform is performed using the same mother wavelet on an unknown sample, and a value of a wavelet expansion coefficient related to the characteristic absorption spectrum at the coefficient position checked in advance is retrieved. The sample can be inspected by checking, with a comparing unit 7, whether the value is approximately the same as a value of an object having the characteristic absorption spectrum.

The wavelet expansion coefficient need only be saved in the personal computer by replacing the value of the wavelet expansion coefficient expressing noise with zero or a small value when it is determined by the inspection that the unknown sample has a characteristic absorption spectrum. Consequently, an inspection on whether a sample has a characteristic absorption spectrum can be realized concurrently with denoising and information compression. By performing an inverse wavelet transform on the saved information-compressed wavelet expansion coefficient, a denoised terahertz wave time waveform having a characteristic absorption spectrum can be restored. Based thereon, imaging of a subject with a favorable SN ratio can be realized.

While the present example is arranged so as to detect a terahertz wave transmitted through the sample 2 with the terahertz wave detecting unit 3, the present example may alternatively be arranged so that a terahertz wave reflected or scattered off of the sample 2 is detected with the terahertz wave detecting unit 3. In addition, while Coiflet4 has been used as the mother wavelet, another mother wavelet may be used as long as such a wavelet is strongly correlated with a terahertz time waveform. Furthermore, while $\log_2 Ls=12$ (where Ls is the number of signal data units) has been used as a wavelet expansion level in the example described above, the level may be set to a value smaller than 12 as long as a wavelet expansion coefficient related to a characteristic absorption spectrum can be found.

The inspection apparatus and method using the present wavelet transform can also be applied to a material having a fingerprint spectrum such as the pharmaceutical products, the hormonal molecules, and the sugars described above.

Second Example

A second example is arranged so as to determine a position and a value of a wavelet expansion coefficient related to a characteristic absorption spectrum without using a threshold as was the case in the first example. The first example determines a wavelet expansion coefficient related to a characteristic absorption spectrum using a threshold, which can be described as a method focusing on the degree of correlation between a terahertz wave time waveform and a mother wavelet or, in other words, the magnitude of the wavelet expansion coefficient. The second example acquires a position and a value of a wavelet expansion coefficient related to a characteristic absorption spectrum by focusing on the frequency (i.e., position of coefficient) of the wavelet expansion coefficient.

Figure 3C:
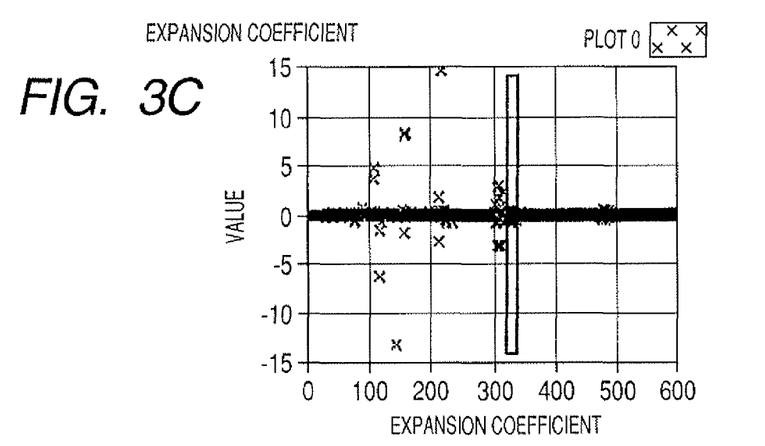

In FIG. 3C, the greater the value of a position of a wavelet expansion coefficient, the higher the frequency of the wave. Therefore, in FIG. 3C, a comparison of a wavelet expansion coefficient at a position near value 500 and a wavelet expansion coefficient at a position near value 100 reveals that the frequency included in the wave is higher for the wavelet expansion coefficient near value 500. Therefore, a position of the wavelet expansion coefficient is specified instead of a value of the wavelet expansion coefficient, the value of the wavelet expansion coefficient at the position is changed to zero and an inverse wavelet transform is performed, and a Fourier transform is subsequently performed to check whether a change has occurred in a characteristic absorption spectrum. In this case, only one position of the wavelet expansion coefficient may be changed to zero, or a position range may be specified such as from value 550 to value 600, whereby all wavelet expansion coefficient values therein are changed to zero. Alternatively, the specification need not be limited to one range and a plurality of ranges may be specified. In any case, a wavelet expansion coefficient related to a characteristic absorption spectrum is narrowed down and identified in this manner.

While the second example differs from the first example in the method of finding a position and a value of a wavelet expansion coefficient related to a characteristic absorption spectrum, other aspects of the second example are the same as the first.

Other Examples

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). Any storage medium may be used as long as the program to be executed by the computer can be stored therein. Any storage medium may be used as long as the program to be executed by the computer can be stored therein.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-316415, filed Dec. 12, 2008, and Japanese Patent Application No. 2009-260108, filed Nov. 13, 2009, which are hereby incorporated by reference herein in their entirety.

What is claimed is:

1. An inspection apparatus for inspecting a subject, comprising:
    an irradiating unit constructed to irradiate the subject with a terahertz wave;
    a detecting unit constructed to detect a terahertz wave obtained from the subject;
    a transforming unit constructed to perform a wavelet transform on a time waveform of the terahertz wave obtained using the terahertz wave detected by the detecting unit, in order to obtain a wavelet expansion coefficient;
    a selecting unit constructed to select a wavelet expansion coefficient corresponding to a desired spectrum from a plurality of wavelet expansion coefficients which are obtained using a reference object having a characteristic part of a spectrum in a terahertz range and which correspond to a part of a frequency having a characteristic spectrum and which are stored in advance in a memory unit; and
    a comparing unit constructed to compare values of the wavelet expansion coefficients, which are values of the wavelet expansion coefficient obtained by the transforming unit and the wavelet expansion coefficient obtained by the selecting unit, corresponding to the part of the frequency having the characteristic spectrum.

2. The inspection apparatus according to claim 1, wherein the inspection apparatus further comprises a determining unit for determining, based on a result obtained by the comparing unit, whether the subject is the reference object or not.

3. An inspection method for inspecting a subject, comprising:
    irradiating the subject with a terahertz wave;
    detecting a terahertz wave obtained from the subject;
    performing a wavelet transform on a time waveform of the terahertz wave obtained using the terahertz wave detected in the detecting step, in order to obtain a wavelet expansion coefficient;
    selecting a wavelet expansion coefficient corresponding to a desired spectrum from a plurality of wavelet expansion coefficients which are obtained using a reference object having a characteristic part of a spectrum in a terahertz range and which correspond to a part of a frequency having a characteristic spectrum and which are stored in advance in a memory unit; and
    comparing values of the wavelet expansion coefficients, which are values of the wavelet expansion coefficient obtained in the transforming step and the wavelet expansion coefficient obtained in the selecting step, corresponding to the part of the frequency having the characteristic spectrum.

4. The inspection method according to claim 3,
the inspection method further comprising determining, based on a result obtained in the comparing step, whether the subject is the reference object or not.

5. A computer-readable storage medium storing a program that causes a computer to execute the inspection method described in claim 3.

6. An extraction method for extracting, from a reference object having a characteristic part of spectrum, an expansion coefficient related to the characteristic part of spectrum, the extraction method comprising:
acquiring the waveform of a terahertz wave reflected or scattered off of or transmitted through the reference object;
performing a wavelet transform on a terahertz time waveform acquired in the acquiring step;
performing an inverse wavelet transform on a portion of expansion coefficients in the wavelet transform, including setting a threshold when specifying the portion of the expansion coefficients; and
performing a Fourier transform on the terahertz time waveform acquired in the inverse-transforming step,
wherein the inverse-transforming step and the Fourier transforming step are repeatedly performed while changing the portion of the expansion coefficients, and
wherein a value of an expansion coefficient that is equal to or greater than the set threshold is replaced by zero.

7. An extraction method for extracting, from a reference object having a characteristic part of spectrum, an expansion coefficient related to the characteristic part of spectrum, the extraction method comprising:
acquiring the waveform of a terahertz wave reflected or scattered off of or transmitted through the reference object;
performing a wavelet transform on a terahertz time waveform acquired in the acquiring step;
performing an inverse wavelet transform on a portion of expansion coefficients in the wavelet transform, including setting a threshold when specifying the portion of the expansion coefficients; and
performing a Fourier transform on the terahertz time waveform acquired in the inverse-transforming step,
wherein the inverse-transforming step and the Fourier transforming step are repeatedly performed while changing the portion of the expansion coefficients, and
wherein a value of an expansion coefficient that is equal to or smaller than the set threshold is replaced by zero.

8. An extraction apparatus for extracting, from a reference object having a characteristic part of spectrum, an expansion coefficient related to the characteristic part of spectrum, the extraction apparatus comprising:
an acquiring unit constructed to acquire the waveform of a terahertz wave reflected or scattered off of or transmitted through the reference object;
a transform unit constructed to perform a wavelet transform on a terahertz time waveform acquired by the acquiring unit;
an inverse transform unit constructed to perform an inverse wavelet transform on a portion of expansion coefficients in the wavelet transform, including setting a threshold when specifying the portion of the expansion coefficients; and
a Fourier transform unit constructed to perform a Fourier transform on the terahertz time waveform acquired by the inverse transform unit,
wherein the inverse-transforming and the Fourier transforming are repeatedly performed while changing the portion of the expansion coefficients, and
wherein a value of an expansion coefficient that is equal to or greater than the set threshold is replaced by zero.

9. An extraction apparatus for extracting, from a reference object having a characteristic part of spectrum, an expansion coefficient related to the characteristic part of spectrum, the extraction apparatus comprising:
an acquiring unit constructed to acquire the waveform of a terahertz wave reflected or scattered off of or transmitted through the reference object;
a transform unit constructed to perform a wavelet transform on a terahertz time waveform acquired by the acquiring unit;
an inverse transform unit constructed to perform an inverse wavelet transform on a portion of expansion coefficients in the wavelet transform, including setting a threshold when specifying the portion of the expansion coefficients; and
a Fourier transform unit constructed to perform a Fourier transform on the terahertz time waveform acquired by the inverse transform unit,
wherein the inverse-transforming and the Fourier transforming are repeatedly performed while changing the portion of the expansion coefficients, and
wherein a value of an expansion coefficient that is equal to or smaller than the set threshold is replaced by zero.

* * * * *